United States Patent
Wehrli (10) Patent No.: US 10,092,488 B1
(45) Date of Patent: *Oct. 9, 2018

(54) SYSTEM AND METHOD FOR REDUCING PLAQUE ON TEETH

(71) Applicant: Janet M. Wehrli, Omaha, NE (US)

(72) Inventor: Janet M. Wehrli, Omaha, NE (US)

( * ) Notice: Subject to any disclaimer, the term of this patent is extended or adjusted under 35 U.S.C. 154(b) by 131 days.

This patent is subject to a terminal disclaimer.

(21) Appl. No.: 15/530,015

(22) Filed: Nov. 18, 2016

Related U.S. Application Data (63) Continuation-in-part of application No. 14/121,414, filed on Sep. 3, 2014, now Pat. No. 9,498,414, which is a continuation-in-part of application No. 12/380,972, filed on Mar. 6, 2009, now abandoned, which is a continuation-in-part of application No. 11/505,167, filed on Aug. 16, 2006, now abandoned.

(60) Provisional application No. 60/787,145, filed on Mar. 30, 2006.

(51) Int. Cl.
| | |
|---|---|
| *A61Q 11/00* | (2006.01) |
| *A61K 8/92* | (2006.01) |
| *A61K 45/06* | (2006.01) |
| *A61K 35/644* | (2015.01) |
| *A61K 33/42* | (2006.01) |
| *A61K 8/19* | (2006.01) |

(52) U.S. Cl.
CPC ............... *A61K 8/19* (2013.01); *A61K 8/922* (2013.01); *A61K 8/925* (2013.01); *A61Q 11/00* (2013.01); *A61K 2800/40* (2013.01)

(58) Field of Classification Search
CPC .. A61Q 11/00; A61K 35/644; A61K 2300/00; A61K 8/24
See application file for complete search history.

(56) References Cited

U.S. PATENT DOCUMENTS

| | | | |
|---|---|---|---|
| 4,148,872 A | 4/1979 | Wagenknecht et al. | 424/48 |
| 4,150,112 A | 4/1979 | Wagenknecht et al. | 424/48 |
| 4,156,715 A | 5/1979 | Wagenknecht et al. | 424/48 |
| 4,157,385 A | 6/1979 | Wagenknecht et al. | 424/48 |
| 4,159,315 A | 6/1979 | Wagenknecht et al. | 424/48 |
| 4,161,517 A | 7/1979 | Wagenknecht et al. | 424/48 |
| 4,225,579 A | 9/1980 | Kleinberg | 424/48 |
| 4,229,485 A | 10/1980 | Brown et al. | 426/305 |
| H83 H | 7/1986 | Poletto et al. | 424/49 |
| 5,249,570 A | 10/1993 | Cox | 128/206.28 |
| 5,405,836 A | 4/1995 | Richar et al. | 514/23 |
| 5,455,024 A | 10/1995 | Winston et al. | 424/52 |
| 5,693,334 A | 12/1997 | Miskewitz | 424/440 |
| 5,944,516 A | 8/1999 | Deshaies | 433/1 |
| 5,993,786 A | 11/1999 | Chow et al. | 424/49 |
| 6,014,950 A | 1/2000 | Rogers | 119/710 |
| 6,050,224 A | 4/2000 | Owens | 119/710 |
| 6,309,676 B1 | 10/2001 | Lewandowski | 424/754 |
| 6,405,681 B1 | 6/2002 | Ward | 119/707 |
| 6,509,007 B2 | 1/2003 | Rajaiah et al. | 424/53 |
| 6,610,276 B2 | 8/2003 | Melman | 424/57 |
| 6,649,147 B1 | 11/2003 | Ye et al. | 424/49 |
| 6,669,928 B1 | 12/2003 | Gurol | 424/49 |
| 6,685,971 B2 | 2/2004 | Xu | 424/725 |
| 6,827,041 B2 | 12/2004 | Hague et al. | 119/709 |
| 6,886,497 B1 | 5/2005 | Hague | 119/710 |
| 6,905,673 B2 | 6/2005 | Rajaiah et al. | 424/49 |
| 6,997,708 B2 | 2/2006 | Allred et al. | 433/80 |
| 7,013,838 B2 | 3/2006 | Hague | 119/710 |
| 7,022,314 B2 | 4/2006 | Barabolak et al. | 424/48 |
| 2003/0113276 A1 | 6/2003 | Rajaiah et al. | |
| 2003/0124230 A1 | 7/2003 | Zielinski | |
| 2003/0175326 A1 | 9/2003 | Thombre | 424/442 |
| 2003/0206948 A1 | 11/2003 | Gergely et al. | 424/465 |
| 2004/0057910 A1 | 3/2004 | Lee et al. | |
| 2004/0101493 A1 | 5/2004 | Scott et al. | 424/49 |
| 2004/0101494 A1 | 5/2004 | Scott et al. | |
| 2004/0118360 A1 | 6/2004 | Hague et al. | |
| 2004/0120900 A1 | 6/2004 | Arsenault | |
| 2004/0244720 A1 | 12/2004 | Jia | |
| 2005/0008584 A1 | 1/2005 | Montgomery et al. | |
| 2005/0071927 A1 | 4/2005 | Hague et al. | |
| 2005/0106111 A1 | 5/2005 | Castor et al. | |
| 2005/0152851 A1 | 7/2005 | Kaminski | |
| 2005/0260544 A1 | 11/2005 | Jones et al. | |
| 2006/0088482 A1 | 4/2006 | Wulknitz et al. | |
| 2006/0239938 A1 | 10/2006 | Perechocky | |
| 2006/0286044 A1 | 12/2006 | Robinson et al. | |

OTHER PUBLICATIONS

Waters, David. Tooth Wear. Waters Orthodontics. Retrieved on May 19, 2014. pp. 1-2.

"Plaque Prevention is hey to Preventing Periodontal Disease", Eschner, Merial Veterinary Services.

*Primary Examiner* — Tracy Liu (74) *Attorney, Agent, or Firm* — James D. Welch (57) ABSTRACT

A system and method which enables application of a material to teeth (and gums), which material remains in contact with, and adheres to, said teeth and gums for a period long enough to neutralize acids in dental plaque biofilm, inhibit plaque from adhering to teeth and gums, encourage removal of dental plaque, and form a barrier between the teeth and gums and the oral environment.

11 Claims, 2 Drawing Sheets

SYSTEM AND METHOD FOR REDUCING PLAQUE ON TEETH

This Application is a CIP of Co-Pending application Ser. No. 14/121,414 Filed Sep. 3, 2014, which is a CIP of Ser. No. 12/380,972, Filed Mar. 6, 2009, which was a CIP of Ser. No. 11/505,167 Filed Aug. 16, 2006, and there via Claims Benefit of Provisional Application No. 60/787,145 Filed Mar. 30, 2006.

TECHNICAL FIELD

This invention relates to means for controlling plaque on teeth, and more particularly a method which enables application of a material to teeth (and gums), which material remains in contact with, and adheres to, said teeth and gums for a period long enough to neutralize acids in dental plaque biofilm, inhibit plaque from adhering to teeth and gums, encourage removal of dental plaque, and form a barrier between the teeth and gums and the oral environment.

BACKGROUND

In humans it is known that benefits are associated with personal cleansing of teeth, and gums, after eating. For instance, brushing can remove acid containing plaque which promotes tooth decay and breath odor. However, brushing is often not possible and many people substitute chewing gum and the like. While chewing gum and the like does provide benefit, such does not neutralize teeth, and gum tissue degrading acids for a prolonged period. Even chewing gums which contain alkaline materials, (ie. sodium bicarbonate), fail to beneficially increase the pH in an oral cavity for a prolonged period, as saliva flow dilutes and dissolves it and then it is quickly swallowed. Therefore present invention specifically does not teach use of chewing gum. It is noted that a neutral pH of 7.0, or at least a pH above about 6 is desirable where the goal is prevention of formation, or reduction in already formed existing plaque.

In animals, (eg. dogs and cats), the above recited approaches of cleaning teeth, (ie. brushing and gum chewing), are not usually convenient or even possible to practice, and approaches to controlling teeth cleanliness and preventing associated pet breath odor usually take the form of providing treated foods or mechanically abrasive chewing systems. Improved methodology of cleaning animal mouths to promote plaque removal and freshened breath thereof would provide utility.

A Search of Patents provided:

U.S. Pat. No. 6,309,676 to Lewandowski describes a Pet Breath Ameliorator involving coating the pets food with pure natural garlic.

U.S. Pat. No. 6,050,224 to Owens describes a Therapeutic Chew Device for Cleaning Teeth and Breath of Dogs. Said device comprises a plurality of polyester yarns with knots near opposite a rope made of rawhide impregnated with activated charcoal. The later component serves to freshen a dogs breath as it chews the device.

U.S. Pat. No. 5,405,836 to Richard et al. describes Pet Foods such as biscuits, which contain Water Soluable Zinc Compound Coating for Controlling Malodorous Breath.

U.S. Pat. No. 5,944,516 to Deshaies describes an Animal Tooth Cleaning Device and Method. The Device comprises a core element having a plurality of brushes extending therefrom which protrude as an animal chews it.

U.S. Pat. No. 6,014,950 to Rogers describes a rolled or folded Terry cloth Dog Teething Toy which can be saturated with water and frozen.

U.S. Pat. No. 5,249,570 to Cox describes an Equine/Canine Hemoglobin-Oxygen Training Mask.

Patents and Published Application to and by Hague which describe Bleached Expanded Pigskin and Products such as Animal Chews are:
U.S. Pat. No. 6,827,041;
U.S. Pat. No. 6,886,497;
U.S. Pat. No. 7,013,838;
US2004/0118360; and
US2005/0071927.

Patents which describe antiplaque compositions and the like are:

Patent No. H83 to Poletto et al. describes dental antiplaque agents and inhibitors of connective tissue disease.

U.S. Pat. No. 6,669,928 to Gurol describes a peridontal composition, which can be a glycerin-free stable gel or paste capable of withstanding high pH environments without degradation.

U.S. Pat. Nos. 4,159,315; 4,157,385; 4,156,715; 4,150,112 and 4,148,872 to Wagenknecht, deceased et al. describe plaque inhibiting composition and method in the form of chewing gum.

U.S. Pat. No. 6,610,276 to Melman describes multi-functional dental composition containing acetic acid for preventing dental plaque, including application to animal teeth.

U.S. Pat. Nos. 6,509,007 and 6,905,673 to Rajaiah et al. describe oral care kits and compositions containing polybutene.

U.S. Pat. No. 5,693,334 to Miskewitz describes chewing gum product comprising gum with encapsulated sodium bicarbonate, a peroxide compound, a bulk sweetener and a flavorant, with dental health benefits.

U.S. Pat. No. 5,455,024 to Winston et al. describes dentifrices containing zinc oxide particles and sodium bicarbonate.

U.S. Pat. No. 7,022,314 to Barabolak et al. describes antiplaque emulsions comprising surfactant, emulsifier and triclosan, and products containing same.

U.S. Pat. No. 6,649,147 to Ye et al. describes a delivery system for oral care compositions comprising organosiloxane resins using a removable backing strip and methods of their use.

U.S. Pat. No. 6,997,708 to Allred et al. describes treatment compositions and strips having a solid adhesive layer and treatment gel adjacent thereto.

U.S. Pat. No. 4,225,579 to Kleinberg describes means and method for improving defenses against caries.

U.S. Pat. No. 5,993,786 to Chow et al. describes anti-carious chewing gums, gels, toothpastes and dentifrices.

U.S. Pat. No. 6,685,971 to Xu et al. describes a method and composition, which can contain an edible wax, for repairing and promoting regeneration of mucosal tissue in the gastrointestinal tract.

Published Application No. 2006/0088482 by Wulknitz et al. describes an oral and dental agent.

Published Application No. 2004/0101493 by Scott et al. describes chewable solid unit dosage forms and methods for delivery of active agents into occlusal surfaces of teeth. This Published Application also describes use of surfactants which decrease adherence of a composition to teeth and gums.

Published Application No. 2005/0008584 by Montgomery is disclosed as it was identified by the Examiner in prosecuting Parent application Ser. No. 11/505,167 and describes application of sodium percarbonate in an oral composition. Montgomery 584, it is focused on teeth whitening. While whiter teeth is a side effect of the present invention, that is not the focus thereof. The present invention has as a primary focus the reducing plaque on mammalian teeth.

U.S. Pat. No. 4,229,486 to U.S. Pat. No. 4,229,485 to Brown as it was identified by the Examiner in prosecuting Parent application Ser. No. 11/505,167.

Published Application No. 2004/0244720 by Jia is disclosed as it was identified by the Examiner in prosecuting Parent application Ser. No. 11/505,167.

Published Application No. 2005/0152851 by Kaminski is disclosed as it describes a stick of semi-hard dentifrice containing sodium bicarbonate as an abrasive. This reference describes applying a sodium bicarbonate containing semi-hard dentifrice onto to teeth, then brushing it off. As opposed to the present invention, no suggestion that the sodium bicarbonate should remain in place for a prolonged period is disclosed. Rather, the sodium bicarbonate is described as being an abrasive to aid with successful brushing.

Published Application No. 2003/0124230 by Zielinski is disclosed as it mentions reducing bad breath.

U.S. Pat. No. 6,405,681 to Ward is disclosed as it describes an animal chew toy with a reservoir for containing liquid. Further, Ward 681 discloses a Chew Toy which can dispense a dentifrice when chewed by a dog, but it does not identify other dispensing approaches.

U.S. Pat. No. 4,151,517 to Wagenknecht, deceased et al. is disclosed as it was identified by the Examiner in prosecuting Parent application Ser. No. 11/505,167.

Published Application No. 2003/0206948 by Geregly et al. is disclosed as it was identified by the Examiner in prosecuting Parent application Ser. No. 12/380,972.

Additional Published Patent Applications which were cited in the prosecution of the Parent Applications are:
2005/0106111 by Castor et al.;
2005/0260544 by Jones et al;
2004/0057910 by Lee et al.;
2006/0286041 by Robinson;
2006/0239938 by Perchocky; and
2003/0113276 by Rajaiah et el.

Published Application No. 2003/0175326 by Thombre is also disclosed.

It is also disclosed that Merial Inc. produces a product called "ORAVET" that comprises a polymer that is applied to pet teeth to prevent formation of plaque.

It is also known that various animals have teeth with characteristics that are genetically designed for various functions. For example, horses and cows have teeth suited for grinding whereas carnivorous animals such as cats and dogs have teeth suited to ripping and tearing. An approach to inhibiting plaque formation which is applicable to all manner of teeth would therefore provide utility. It is noted that the present invention utilizes a composition of material with a pH preferably above about 7.0 that, in use, forms a barrier between teeth and gums, with respect to an oral environment, in a manner that maintains said material in contact with the teeth for a period of at least an hour. Strong acid is not involved at all.

Also identified is a Published Application by Lawlor, No. 2003/0103914 Published 06/2003 which discloses the practice of using sodium bicarbonate to abrasively remove plaque. This reference does not, however, disclose intentionally maintaining the sodium bicarbonate in contact with teeth and gum, in a substantially undiluted form, for hours and longer, before optional removal.

It is also noted that cited reference Thombre US2003/0175326 does not make any mention of a "barrier", both Scott et al. US2004/0101493 and Gergely et al. US2003/0206948 do use the word "barrier", but not at all in the context of the Present Application.

It is also noted that Scott (Published Application 2004/0101493) specifies its components "By Weight", whereas the Present Claims state "By Volume". And, Gangly (Published Application 2003/0206948) involves use of "Chewing Tablets".

A need remains for a system and method which would enable application of a material to teeth and gums, which material remains in contact with, and adheres to, said teeth and gums for a period long enough to neutralize acids in dental plaque biofilm, inhibit plaque from adhering to teeth and gums, encourage removal of dental plaque, and form a barrier between the teeth and gums and the oral environment, which barrier preferably remains in place for days if not intentionally removed.

DISCLOSURE OF THE INVENTION

The present invention is a method of protecting teeth in an oral environment, comprising the steps of:
 a) providing a composition of matter that consists of, by total volume, or equivalent by weight:
  >0.0-4/16, nominally 1/8, edible adherent matter;
  8/16-12/16 oil, nominally 5/8; and
  2/16-6/16, nominally 2/8 plaque inhibiting sodium and/or potassium bicarbonate;
 each of said amounts being selected so that the total adds to 100%; and which:
  adheres to teeth and serves as a barrier between teeth and the oral environment;
  inhibits plaque from adhering to teeth; and
  reduces plaque on teeth when left in place for hours rather than minutes;
and which composition of matter has a pH of at least 6.0. Said method continues with:
 b) applying said composition of matter having the properties listed in step a) to the teeth of a mammal such that a majority thereof adheres to and remains in place on said mammalian teeth as a barrier between said teeth and oral environment for a period of time of at least one hour;
such that adherence of new plaque is inhibited, and/or existing plaque is reduced.

Said method is distinguished by the forming of, and presence of said plaque preventing and/or reducing barrier between said teeth and said oral environment for hours rather than minutes, and does not require use of any selection from the group consisting of:
 chewing gum;
 mechanical abrasion;
 surfactant;
 polybutene;
 a backing strip; and
 a brush.

Said method can involve that the edible adherent material is at least one selection from the group consisting of:
 beeswax;
 honey;
 gum;
 lanolin;
 tallow;
 candelilla;

soy;
ceresin;
montan;
paraffin;
ethylenic polymers;
chlorinated naphthalenes;
Fisher-Tropsch wax;
castor wax;
glycowax;
carnuba wax.

Said method can involve that the oil is at least one selection from the group consisting of:
castor oil;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
sesame oil;
soybean oil;
sunflower oil;
acia oil;
blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
quinoa oil;
ramtil oil;
rice bran oil;
thistle oil;
wheat germ oil;
radish oil;
rapeseed oil.

Said method can involve that the composition of matter further consists of a flavoring wherein the flavoring is at least one selection from the group consisting of:
almond flavoring;
beef flavoring;
chicken flavoring;
turkey flavoring;
lamb flavoring;
fish flavoring;
liver flavored;
egg flavoring;
dairy flavoring;
mint flavoring;
orange flavoring.

An alternative recital of a present invention method of protecting teeth in an oral environment comprises:
a) providing a composition of matter that does not require any selection from the group consisting of:
chewing gum;
mechanical abrasion;
surfactant;
polybutene;
a backing strip; and
a brush;
but comprises a composition of matter that consists of, by total volume or weight:
approximately >0.0-4/16, nominally 1/8, edible adherent matter;
approximately 8/16-12/16 oil, nominally 5/8; and
approximately 2/16-6/16, nominally 2/8 plaque inhibiting sodium and/or potassium bicarbonate;
each of said amounts being selected so that the total adds to 100%; and which:
said composition of matter including, in at least one of the components, at least one selection from the group consisting of:
medicinals;
fragrances;
flavoring;
preservatives;
colorings;
at least one component which absorbs and/or diminishes toxins;
almond flavoring;
beef flavoring;
chicken flavoring;
turkey flavoring;
lamb flavoring;
fish flavoring;
liver flavored;
egg flavoring;
dairy flavoring;
mint flavoring;
orange flavoring;
castor oil;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
sesame oil;
soybean oil;
sunflower oil;

acia oil;
black currant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
quinoa oil;
ramtil oil;
rice bran oil;
thistle oil;
wheat germ oil;
radish oil; and
rapeseed oil;
beeswax;
honey;
gum;
lanolin;
tallow;
candelilla;
soy;
ceresin;
montan;
paraffin;
ethylenic polymers;
chlorinated naphthalenes;
Fisher-Tropsch wax;
castor wax;
glycowax; and
carnuba wax;
b) said method further comprising applying some of said composition of matter to teeth of a mammal such that a majority thereof adheres to and remains in place on said mammalian teeth as a barrier between said teeth and oral environment for a period of time of at least one hour;
such that adherence of new plaque is inhibited, and/or existing plaque is reduced.

As presented in the Parent application Ser. Nos. 12/380,972 and 14/121,414, the present invention includes a method of controlling plaque on teeth which comprises the basic steps of providing a system comprising means for containing a composition of material which:
adheres to teeth and serves as a barrier between teeth and gums, and the environment;
inhibits plaque from adhering to teeth; and
optionally dissolves and/or absorbs plaque.
Said system can further serve to neutralize acids and freshen breath.

Said system further comprises means for dispensing said composition of material for application onto teeth, wherein said means for dispensing said material being selected from the group consisting of:
a tube comprising means for dispensing said composition of material onto teeth, said dispensing means comprising a means for causing said material to extend from said tube in a manner allowing it to be placed into contact with teeth;
a tub of composition for application via fingers or the like;
a means for spraying said material at teeth.
Said system dispensing said composition of material can further comprise a means for self-application, such as providing the material in a chewable system.
Said method further involves causing said system to mediate application of said material to teeth such that it remains in place for a period of time, in a substantially undiluted form, sufficient to remove plaque.
Said method can be practiced on a human, or on any animal, but typical practice on animals will involve application to cat or dog teeth.
Said method can provide that the material is selected to comprise plaque inhibiting material, (eg. beeswax and sodium or potassium bicarbonate), and the material can further comprise at least one selection from the group consisting of oils, fragrances, preservatives, flavoring, colorings, medicinals and decay inhibiting materials. It is noted also that Beeswax provides negative ions when warmed, and presence in a typical mammalian's mouth will cause the effect. Most other waxes are not known to do so.
The composition of material, which:
adheres to teeth and serves as a barrier between teeth and gums, and the environment;
inhibits plaque from adhering to teeth; and
optionally dissolves and/or absorbs plaque.
can be fabricated by a method comprising the steps of:
a) providing an edible wax and heating it until it becomes a liquid;
b) entering a component which serves to inhibit plaque from forming on teeth and causing it to become substantially uniformly distributed therewithin;
c) cooling the result.
Said method can further involve adding at least one selection from the group consisting of one or more oils, fragrances, flavors, preservatives, colorings and medicinals before cooling in step c.
Said method can also include providing at least one component which absorbs, (eg. diminishes), toxins.
As presented in Parent application Ser. No. 14/121,414, said composition of material can comprise beeswax in functional combination with a plaque inhibiting ingredient, and can be comprise, by volume, approximately:
1/8 edible adherent material, such as beeswax, (one part);
5/8 oil (five parts); and
2/8 plaque inhibiting material (two parts).
(It is noted that the 5/8 oil can include medicinals and/or other components and that, for instance, honey or a gum can be substituted for, or added to the 1/8 edible adherent material).
The plaque inhibiting material can be, but is not limited to, sodium or potassium bicarbonate, and white beeswax is a preferred as a non-limiting edible adherent material. A decay inhibiting material can be fluoride or a functionally similar material.
The step of providing an edible adherent material can involve providing at least one selection from the group consisting of:

beeswax;
honey;
gum;
lanolin;
tallow;
carnuba;
candelilla;
soy;
ceresin;
montan;
paraffin;
ethylenic polymers;
chlorinated naphthalenes;
Fisher-Tropsch;
castor wax;
glycowax;
carnuba wax;
in combination with an edible oil. Oils which can be applied in practice of the methodology can be selected from, but are not limited by, the group consisting of:

Nut Oils:
almond oil;
cashew oil;
hazelnut oil;
macadamia oil;
pecan oil;
pistachio oil;
walnut oil;

Other Edible Oils:
coconut oil;
corn oil;
cottonseed oil;
canola oil;
olive oil;
palm oil;
peanut oil;
safflower oil;
sesame oil;
soybean oil;
sunflower oil;
acia oil;
blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
quinoa oil;
ramtil oil;
rice bran oil;
thistle oil;
wheat germ oil;
radish oil;
rapeseed oil.

Flavorings which can be applied in practice of the methodology can be selected from the group consisting of:
almond flavored;
beef flavored;
chicken flavored;
turkey;
lamb flavored;
fish;
liver;
egg;
dairy flavored;
mint;
orange.

Any flavor which a human or animal would not reject can be used.

The step of providing a plaque inhibiting ingredient can involve providing at least one selection from the group consisting of:
sodium bicarbonate;
potassium bicarbonate; and
other buffering salt;
and can involve providing a decay inhibiting material such as fluoride.

Said method can also involve the step of applying said material to said teeth via:
application from a stick of material;
application by use of finger;
application by use of an applicator held by fingers;
application via a spray;
application by syringe; and
application via applying a strip containing said material to said teeth;
application via use of an application brush or the like, as opposed to an toothbrush brush which serves to remove material.

Said system dispensing said composition of material can further comprise a means for animal self-application, such as providing the material in a chewable system.

Further, while actually counter to the focus of present invention, said method can further comprise, after some relatively long time period, (eg. hours as opposed to minutes), after application of said material to teeth and/or gums, the step of removing said material applied to said teeth and/or gums by an approach that results in removal of plaque removed from teeth along therewith. This can be accomplished by, for instance brushing or wiping. While prior art describes brushing with sodium bicarbonate, which acts as an abrasive agent, said prior art does not describe intentionally maintaining the sodium bicarbonate in contact with teeth and gums, in a substantially undiluted form, for hours and longer, before optional removal.

Also, it is noted that the methodology can further include providing medication in said material for entry to a mammal's system via oral mucosa.

The present invention, being very portable, can be conveniently utilized whenever desired.

Additional recitation in this Application provides that present Application presents Claims to a method of reducing plaque on mammalian teeth in an oral environment that does not involve chewing gum or require mechanical abrasion or surfactant, but rather functions by maintaining contact of a composition of matter with teeth such that a barrier is formed thereby between said teeth and said oral environment for a period of at least an hour, comprising the steps of:

a) providing a system comprising a container for a composition of material, which composition of material:
  adheres to teeth and serves as a barrier between teeth, and the oral environment;
  inhibits plaque from adhering to teeth; and
    reduces and/or absorbs plaque on teeth when left in place for hours rather than minutes;
which composition of matter does not require an acid component and presents with a pH of at least 6.0.

Said method proceeds with:

b) fabricating a composition of material meeting the requirements listed in step a) and placing said composition of material into said container;

c) dispensing some of said composition of material having the properties listed in step a) from said container therefore, and causing it to be applied to the teeth of a mammal such that a majority thereof adheres to and remains in place on said mammalian teeth for a period of time of at least one hour in an undiluted form;

such that adherence of new plaque is inhibited, and/or existing plague is reduced and/or absorbed.

Said method is distinguished by the forming of, and presence of, said plaque preventing and/or reducing barrier between said teeth and said oral environment for hours rather than minutes, and the absence of any requirement for the use of chewing gum or mechanical abrasion or surfactant.

Said method can further comprise a step d, said step d being selected from the group consisting of:
  d) repeating step c) at last once a day for at least one week;
  d) repeating step c) for at least two weeks;
  d) repeating step c) at least twice a day;
  d) involves repeating step c) at least twice a day for at least two weeks;
  d) involves repeating step c) at least once a day for more than two weeks.

Said method can involve the composition of material further comprising at least one selection from the group consisting of oils, medicinals, fragrances, flavoring, preservatives and colorings.

Said method can involve that the composition of material that:
  adheres to teeth and serves as a barrier between teeth, and the oral environment;
  inhibits plaque from adhering to teeth; and
    reduces and/or absorbs plaque on teeth when left in place for hours rather than minutes;
is fabricated by a method comprising the steps of:
  a) providing an edible adherent material and heating it until it becomes a liquid;
  b) entering a component which serves to inhibit plaque from forming on teeth and causing it to become uniformly distributed therewithin;
  c) cooling the result.

Said composition fabrication method can which further involve adding at least one selection from the group consisting of one or more oils, medicinals, fragrances, preservatives and colorings before cooling in step.

Said method, as presented in Parent application Ser. No. 14/121,414, can provide that said composition of matter comprises, by total volume of the composition, approximately:
  1/8 beeswax;
  5/8 oil; and
  2/8 plaque inhibiting sodium and/or potassium bicarbonate.

Said method can involve that said oil contains at least one medicinal.

Said fabrication method can involve, in the step of fabricating a composition of material, providing beeswax in functional combination with at least one component that absorbs and/or diminishes toxins.

Said method can involve step b at least one adherent selected from the group consisting of:
  beeswax;
  honey;
  gum;
  lanolin;
  tallow;
  candelilla;
  soy;
  ceresin;
  montan;
  paraffin;
  ethylenic polymers;
  chlorinated naphthalenes;
  Fisher-Tropsch;
  castor wax;
  glycowax;
  carnuba wax;
in combination with an oil.

Said method can involve the oil comprising at least one selection from the group consisting of:
  almond oil;
  cashew oil;
  hazelnut oil;
  macadamia oil;
  pecan oil;
  pistachio oil;
  walnut oil;
  coconut oil;
  corn oil;
  cottonseed oil;
  canola oil;
  olive oil;
  palm oil;
  peanut oil;
  safflower oil;
  sesame oil;
  soybean oil;
  sunflower oil;
  acia oil;
  blackcurrant oil;
  borage oil;
  evening primrose oil;
  amaranth oil;
  apricot oil;
  argan oil;
  avocado oil;
  babassu oil;
  ben oil from moringa oleifera;
  carob oil;
  coriander seed oil;
  false flax oil from coriander seeds;
  grape seed oil;
  hemp oil;
  meadowfoam seed oil;
  mustard oil;
  okra seed oil;
  perilla seed oil;
  pine seed oil;
  poppyseed oil;
  prune kernel oil;

pumpkinseed oil;
quinoa oil;
ramtil oil;
rice bran oil;
thistle oil;
wheat germ oil;
radish oil;
rapeseed oil.

Said method can involve a flavoring also being provided as part of the oil which comprises at least one selection from the group consisting of:
almond flavoring;
beef flavoring;
chicken flavoring;
turkey flavoring;
lamb flavoring;
fish flavoring;
liver flavored;
egg flavoring;
dairy flavoring;
mint;
orange.

Said method can involve the plaque inhibitor that inhibits plaque from adhering to teeth and reduces existing plaque when left in place over an hour, consists of at least one selection from the group consisting of:
sodium bicarbonate;
potassium bicarbonate.

Said method can involve the step of dispensing said composition of material to said teeth involves a selection from the group consisting of:
application from a stick of said composition of material;
application by use of finger;
application by use of an applicator held by fingers;
application via a spray;
application by syringe;
application via applying a strip containing said material to said teeth;
application via an application brush; and
a chewable system which contains said composition of material.

Said method can further comprise the step of removing said composition of material applied to said teeth by an approach that results in removal of plaque dislodged from teeth along therewith for aesthetic purposes.

Said method can further provide that the step of dispensing said composition of material to said teeth involves a selection from the group consisting of:
application from a stick of said composition of material;
application by use of finger;
application by use of an applicator held by fingers;
application via a spray;
application by syringe;
application via applying a strip containing said material to said teeth;
application via an application brush; and
a chewable system which contains said composition of material.

Said method can involve that the mammalian teeth are a selection from the group consisting of:
cat teeth;
dog teeth; and
human teeth.

Said method can involve that said composition of material remains in contact with said teeth for a period sufficiently long to freshen breath, neutralize acids in dental plaque biofilm, inhibit plaque from adhering to teeth, encourage removal of dental plaque, and form a barrier between the teeth and gums, and the oral environment, and even absorb into gums.

Said method can involve said composition of material further comprises medication.

Said method of composition fabrication can involve that said method further comprises, prior to step c, the addition of medicine thereto.

Said method can involve the composition of material further comprises at least one selection from the group consisting of:
acid neutralizing material;
breath freshening material;
at least one medicinal; and
at least one decay inhibiting material.

Said method can involve the composition of material is formulated to include at least one selection from the group consisting of:
acid neutralizing material;
breath freshening material;
at least one medicinal; and
at least one decay inhibiting material.

As also presented in Parent application Ser. No. 14/121,414, another recitation of a present invention method of reducing plaque on mammalian teeth in an oral environment that does not involve chewing gum or require mechanical abrasion or surfactant, but rather functions by maintaining contact of a composition of matter with teeth such that a barrier is formed thereby between said teeth and said oral environment for a period of at least an hour, provides that it comprises the steps of:
a) providing a composition of matter comprising, by total volume, approximately:
⅛ beeswax;
⅝ oil; and
2/8 plaque formation inhibiting sodium and/or potassium bicarbonate;
which composition of matter does not require an acid component and presents with a pH of at least 6.0. which in use:
as a result of the beeswax adhering to teeth, serves as a barrier between teeth and the oral environment;
as a result of the sodium and/or potassium bicarbonate inhibits plaque from adhering to teeth; and
reduces and/or absorbs plaque on teeth when left in place for at least one hour.

Said method continues with:
b) causing said composition of material to be applied to mammalian teeth such that a majority thereof remains in place in an undiluted form for a period of time of at least an hour, with the result being that new plaque is inhibited from forming on said teeth, and at least some existing plaque is caused to be absorbed thereinto;
c) repeating step b) at last once a day for at least one week;
such that production of new plaque is inhibited, and/or existing plaque is reduced and/or absorbed.

Said method is distinguished by the forming of, and presence of said plaque preventing and/or reducing barrier between said teeth and said oral environment for hours rather than minutes, and the absence of any requirement for the use of chewing gum or mechanical abrasion or surfactant.

Said method can involve the composition of material being caused to remain in contact with said teeth for a period of many hours, and a significant amount of existing plaque accumulation on teeth is caused to be reduced and/or absorbed thereinto.

Yet another recitation of a present invention method of reducing plaque on mammalian teeth in an oral environment that functions by maintaining contact of a composition of matter with teeth such that a barrier is formed thereby between said teeth and said oral environment for a period of at least an hour, provides that it comprises the steps of:

a) providing a composition of material, which composition of material that:
   adheres to teeth and serves as a barrier between teeth and the oral environment;
   inhibits plaque from adhering to teeth; and
     reduces plaque on teeth when left in place for hours rather than minutes;

which composition of matter does not require an acid component and presents with a pH of at least 6.0.

Said method continues with:

b) applying said composition of material having the properties listed in step a) to the teeth of a mammal such that a majority thereof adheres to and remains in place on said mammalian teeth as a barrier between said teeth and oral environment for a period of time of at least one hour in an undiluted form;

such that adherence of new plaque is inhibited, and existing plaque is reduced.

Said method is distinguished by the forming of, and presence of said plaque preventing and/or reducing barrier between said teeth and said oral environment for hours rather than minutes, and the absence of any requirement for the use of chewing gum or mechanical abrasion or surfactant.

Any present invention method can provide that the pH of the composition is at least 7.0.

Any present invention method can provide that not only is there no requirement for the use of chewing gum or mechanical abrasion or surfactant, there is no use thereof made.

Any present invention method can involve at least some gum tissue associated with said teeth of said mammal is included within the barrier formed between said teeth and said oral environment. It is noted that a significant amount of gum tissue can actually be coated with present invention composition with beneficial results being provided thereby.

As the Parent 972 Application was held to be deficient in that it did not provide support for negative limitations in the Claims, it is specifically stated at this point herein that the preferred embodiment of the present invention does not involve use of garlic, charcoal, zinc, zinc oxide, sodium percarbonate, brushes, abrasive agents for their abrasive properties, ice, hemoglobin, oxygen, glycerin, acetic acid, citrus acid, vitis acid, (no strong acid is involved in any formulation of the present invention), peanut oil, polybutene, chewing gum, surfactants, emulsifiers, triclosan, removable backing strips, toothpastes, chewable toys, polymers, hexametaphosphate, etc. These, and other extraneous materials and practices are identified in various cited prior art. The present invention functions by providing a barrier between teeth and an oral environment for a period of at least an hour. Any material or practice not required to cause said "barrier" effect and includes a plaque inhibiting and/or reducing or other agent which reduces adherence to teeth is not required by the present invention. Such exclusions as just exemplified are simply not present in the preferred embodiment of the present invention. Neither present in the present invention method is a requirement for removal of the barrier forming agent in the present invention, although optional removal can be practiced, at some time, for aesthetic purposes.

In the foregoing, wherein a barrier is stated to be formed, it is to be understood that said barrier can also involve at least some gum tissue associated with teeth of said mammal be included within the barrier formed between the teeth and said oral environment. It is noted that benefit results where as much gum tissue as it is possible to contain, is contained within said barrier.

The present Application extends description of the composition of matter to involve components in ranges:
   approximately >0.0-4/16, nominally 1/8, edible adherent matter;
   approximately 8/16-12/16 oil, nominally 5/8; and
   approximately 2/16-6/16, nominally 2/8 plaque inhibiting sodium and/or potassium bicarbonate;

each of said amounts being selected so that the total adds to 100%.

The invention will be better understood by reference to Detailed Description Section of this Specification, in combination with the Drawings.

DETAILED DESCRIPTION

Figure 1:
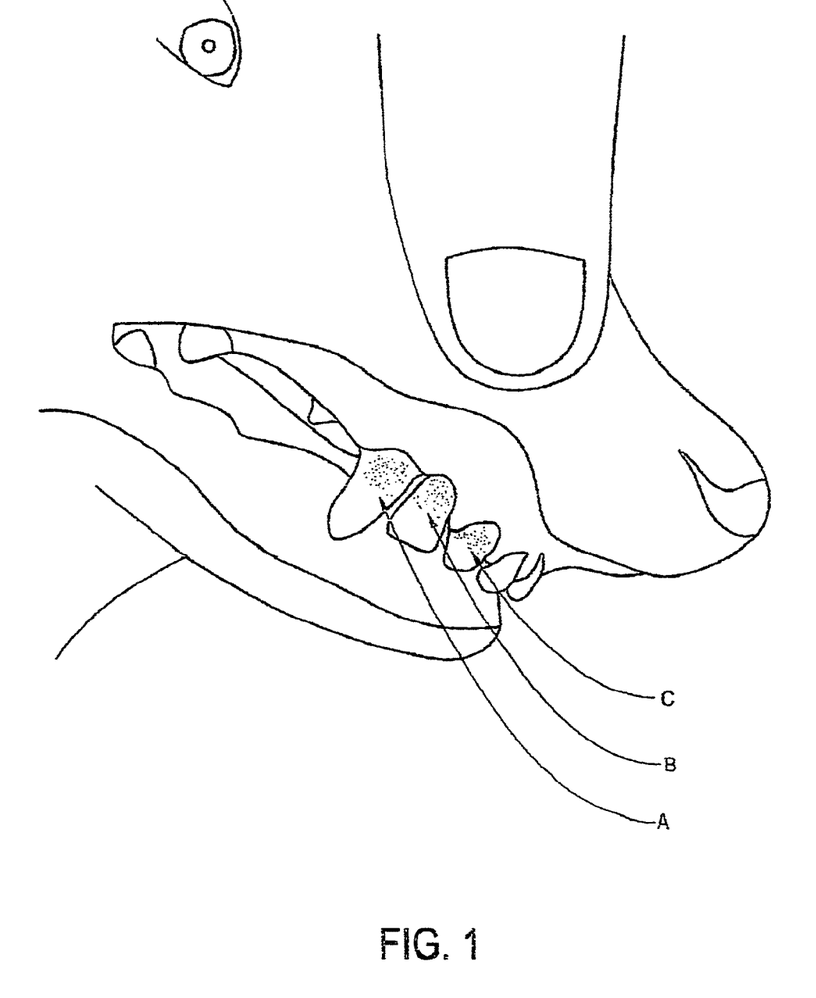
FIG. 1 shows a photo of a dog's teeth before application of a present invention composition of material thereto.
Figure 2:
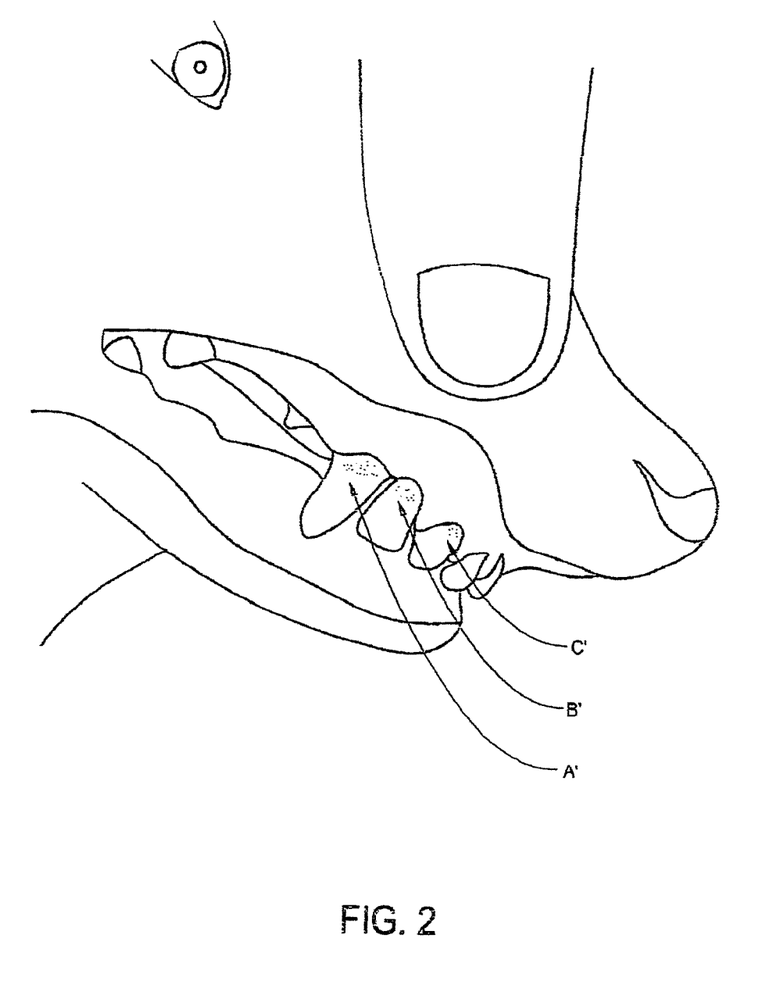
FIG. 2 shows a photo of a dog's teeth after use of a present invention composition of material thereto over a period of two to three weeks.

Turning now to FIGS. 1 and 2, there are shown sketches based on photos of a dog's teeth before and after treatment by a present invention composition of material thereto. The composition used was comprised of, by volume:
   1/8 white beeswax;
   5/8 almond oil, (which can include medicinals or other materials); and
   2/8 sodium bicarbonate;

and was prepared by placing the beeswax and almond oil into a container in a water bath which was heated until said components thoroughly mixed with one another, and then the sodium bicarbonate was added and mixed until it was evenly distributed in the mix.

(Again, it is noted that the 5/8 oil can include medicinals and/or other components and that, for instance, honey or a gum can be substituted for, or added to the 1/8 white beeswax).

Application to the dog's teeth was accomplished by placing present invention composition on the applier's finger and transfer to the dog's teeth there via. Note that FIG. 2 shows that plague present on the dog's teeth in FIG. 1 is reduced. The results depicted correspond to application once or twice a day over period of two to three weeks. The dog's breath was noted to improve in the first week of use.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of protecting teeth in an oral environment, comprising the steps of:
   a) providing a composition of matter that consists of, by total volume:
     >0.0-4/16 edible adherent matter;

8/16-12/16 oil; and
2/16-6/16 plaque inhibiting sodium and/or potassium bicarbonate;
each of said amounts being selected so that the total adds to 100%; wherein said composition of matter:
adheres to teeth and serves as a barrier between teeth and the oral environment;
inhibits plaque from adhering to teeth; and
reduces plaque on teeth when left in place for hours rather than minutes;
and has a pH of at least 6.0; and
b) applying said composition of matter having the properties listed in step a) to the teeth of a mammal such that a majority thereof adheres to and remains in place on said mammalian teeth as a barrier between said teeth and oral environment for a period of time of at least one hour;
said method being distinguished in that it does not comprise any selection from the group consisting of:
chewing gum;
mechanical abrasion;
surfactant;
polybutene;
a backing strip; and
a brush.

2. A method as in claim 1 in which the edible adherent material is at least one selection from the group consisting of:
beeswax;
honey;
gum;
lanolin;
tallow;
candelilla;
soy;
ceresin;
montan;
paraffin;
ethylenic polymers;
chlorinated naphthalenes;
Fisher-Tropsch wax;
castor wax;
glycowax; and
carnuba wax.

3. A method as in claim 1 in which the oil is at least one selection from the group consisting of:
castor oil;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
sesame oil;
soybean oil;
sunflower oil;
acia oil;
blackcurrant oil;
borage oil;
evening primrose oil;
amaranth oil;
apricot nil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
quinoa oil;
ramtil oil;
rice bran oil;
thistle oil;
wheat germ oil;
radish oil; and
rapeseed oil.

4. A method as in claim 1 wherein the composition of matter further consists of a flavoring wherein the flavoring is at least one selection from the group consisting of:
almond flavoring;
beef flavoring;
chicken flavoring;
turkey flavoring;
lamb flavoring;
fish flavoring;
liver flavored;
egg flavoring;
dairy flavoring;
mint flavoring; and
orange flavoring.

5. A method as in claim 1 in which at least one of said components of said composition of matter further consists of at least one selection from the group consisting of fluoride, medicinals, fragrances, flavoring, preservatives and colorings.

6. A method as in claim 1 in which the step of applying said composition of matter to said teeth comprises a selection from the group consisting of:
application from a stick of said composition of matter;
application by use of finger;
application by use of an applicator held by fingers;
application via a spray; and
application by syringe.

7. A method as in claim 1 in which the mammalian teeth are a selection from the group consisting of;
cat teeth;
dog teeth; and
human teeth.

8. A method as in claim 1, in which at least some gum tissue associated with said teeth of said mammal are included within the barrier formed between said teeth and said oral environment.

9. A method as in claim 1 in which the composition of matter further consists of at least one selection from the group consisting of:

acid neutralizing material;
breath freshening material;
at least one medicinal; and
at least one decay inhibiting material.

10. A method as in claim 1, in which the pH is at least 7.0.

11. A method of protecting teeth in an oral environment that does not comprise any selection from the group consisting of: chewing gum; mechanical abrasion; surfactant; polybutene; a backing strip; and a brush; comprising the steps of:
a) providing a composition of matter consisting
but comprises a composition of matter that consists of, by total volume:
approximately >0.0-4/16 edible adherent matter;
approximately 8/16-12/16 oil; and
approximately 2/16-6/16, inhibiting sodium and/or potassium bicarbonate;
each of said amounts being selected so that the total adds to 100%; wherein:
said composition of matter further consists of, in at least one of the components, at least one selection from the group consisting of:
fluoride;
medicinals;
fragrances;
flavoring;
preservatives;
colorings;
at least one component which absorbs and/or diminishes toxins;
almond flavoring;
beef flavoring;
chicken flavoring;
turkey flavoring;
lamb flavoring;
fish flavoring;
liver flavored;
egg flavoring;
dairy flavoring;
mint flavoring;
orange flavoring;
castor oil;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
sesame oil;
soybean oil;
sunflower oil;
acia oil;
black currant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
guinea oil;
ramtil oil;
rice bran oil;
thistle oil;
wheat germ oil;
radish oil; and
rapeseed oil;
beeswax;
honey;
gum;
lanolin;
tallow;
candelilla;
soy;
ceresin;
montan;
paraffin;
ethylenic polymers;
chlorinated naphthalenes;
Fisher-Tropsch wax;
castor wax;
glycowax; and
carnuba wax; and
b) applying some of said composition of matter to teeth of a mammal such that a majority thereof adheres to and remains in place on said mammalian teeth as a barrier between said teeth and oral environment for a period of time of at least one hour;
such that adherence of new plaque is inhibited, and/or existing plaque is reduced.

* * * * *